(12) United States Patent
Morris

(10) Patent No.: US 9,179,921 B1
(45) Date of Patent: Nov. 10, 2015

(54) INFLATABLE BALLOON STENT

(71) Applicant: Michael Christopher Morris, Laredo, TX (US)

(72) Inventor: Michael Christopher Morris, Laredo, TX (US)

( * ) Notice: Subject to any disclaimer, the term of this patent is extended or adjusted under 35 U.S.C. 154(b) by 19 days.

(21) Appl. No.: 13/657,435

(22) Filed: Oct. 22, 2012

Related U.S. Application Data

(60) Provisional application No. 61/550,279, filed on Oct. 21, 2011.

(51) Int. Cl.
| | |
|---|---|
| *A61B 17/12* | (2006.01) |
| *A61M 1/00* | (2006.01) |
| *A61M 25/10* | (2013.01) |
| *A61F 2/04* | (2013.01) |

(52) U.S. Cl.
CPC ..... *A61B 17/12136* (2013.01); *A61B 17/12036* (2013.01); *A61F 2/04* (2013.01); *A61M 1/00* (2013.01); *A61M 2025/1061* (2013.01); *A61M 2025/1086* (2013.01); *A61M 2025/1097* (2013.01)

(58) Field of Classification Search
CPC ...... A61F 2/04; A61F 2/958; A61M 25/1002; A61M 25/1011; A61M 2025/1013; A61M 25/1025; A61M 2025/1097; A61M 2025/1086; A61M 2025/1061; A61B 17/12136; A61B 17/12036

USPC ............ 604/101.01–101.05, 103.06, 103.08, 604/103.01
See application file for complete search history.

(56) References Cited

U.S. PATENT DOCUMENTS

| | | | | |
|---|---|---|---|---|
| 5,792,105 | A * | 8/1998 | Lin et al. .................. | 604/103.01 |
| 5,906,606 | A * | 5/1999 | Chee et al. ..................... | 604/527 |
| 7,806,857 | B2 * | 10/2010 | Khosravi et al. ......... | 604/101.01 |
| 8,702,745 | B2 | 4/2014 | Degen | |
| 2004/0093026 | A1 | 5/2004 | Weidenhagen et al. | |
| 2006/0089596 | A1* | 4/2006 | Ravo ........................ | 604/101.01 |
| 2010/0069878 | A1* | 3/2010 | Parsai et al. .................... | 604/500 |
| 2010/0087781 | A1* | 4/2010 | Adams et al. ............ | 604/101.03 |
| 2013/0190706 | A1 | 7/2013 | Kleiner | |
| 2014/0088622 | A1 | 3/2014 | Rousseau | |

FOREIGN PATENT DOCUMENTS

| | | |
|---|---|---|
| WO | 2012071626 | 6/2012 |
| WO | 2013181686 | 12/2013 |

* cited by examiner

*Primary Examiner* — Theodore Stigell
*Assistant Examiner* — Benjamin Koo
(74) *Attorney, Agent, or Firm* — Plager Schack LLP

(57) ABSTRACT

A medical device consists of a dual lumen catheter with three intra-connecting balloons comprising a balloon stent. The adjustable tissue approximation using negative pressure exerted between device and mucosa of stomach/esophagus/colon with improved injury site isolation via adjustable balloon stent and added potential of negative pressure application to injury site for active healing process and distal feeding potential.

3 Claims, 3 Drawing Sheets

US 9,179,921 B1

INFLATABLE BALLOON STENT

CROSS REFERENCE TO RELATED APPLICATION

The present application claims priority to U.S. Provisional Application Ser. No. 61/550,279, filed on Oct. 21, 2011, the disclosure of which is incorporated herein by reference in its entirety.

BACKGROUND

Numerous serious medical issues arise within the proximal and/or distal aspect of the Gastrointestinal or GI tract. Many of these conditions are related to wall perforation allowing intra luminal content exposure to the abdominal cavity with morbid consequences. Treatment often is difficult and with undesirable outcomes. In the event of post-operative complication of the proximal stomach in the case of a sleeve gastrectomy a staple line dehiscence represents the most feared complication due to the futility of the few available treatment options. Currently the intraluminal expandable metallic covered stents are considered the treatment of choice with a high associated cost and significant complication rate including migration, stomach perforation and inability of removal requiring total gastrectomy.

Staple line dehiscence or leakage can create a state of sepsis which is technically challenging and potential harmful to patients.

Current self-expanding stents have high rates of distal mobility, may cause bleeding, reflux, non-isolation and prolong time to resolution. Also, there may be a high cost associated with the use of a non FDA approved application.

Currently, a non-FDA approved esophageal self-expanding esophageal stent is being used with moderate resolution rates. While this conventional device provides some improvement over prior approaches, it is desirable to provide for improved isolation, distal feeding and negative pressure application which may aid in hastening resolution, recover and potential for prevention. Conventional devices and approaches do not address these desired improvements.

Improvements to these conventional approaches to treatment of conditions within the GI tract are desirable.

BRIEF DESCRIPTION OF THE DRAWINGS

The accompanying drawing figures, which are incorporated in and constitute a part of the description, illustrate several aspects of the present disclosure and together with the description, serve to explain the principles of the present disclosure. A brief description of the figures is as follows.

DESCRIPTION LIST

Figure 1:
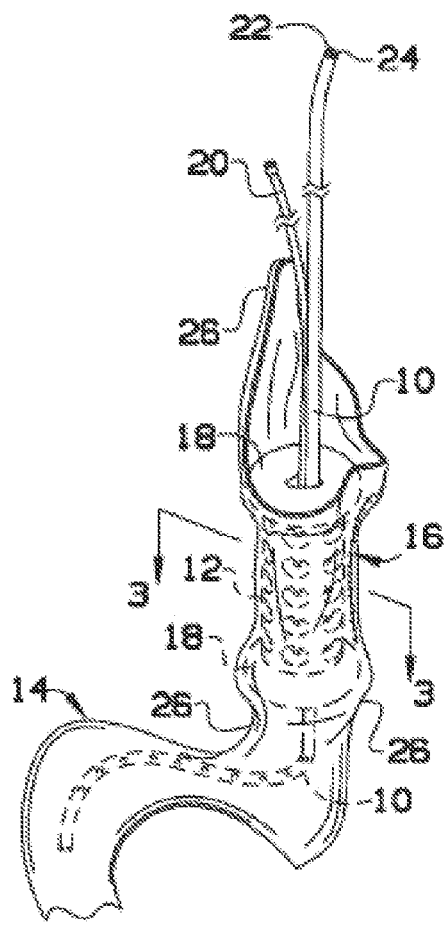
FIG. 1 is a perspective cutaway view of a device according to the present disclosure shown in use.
Figure 2:
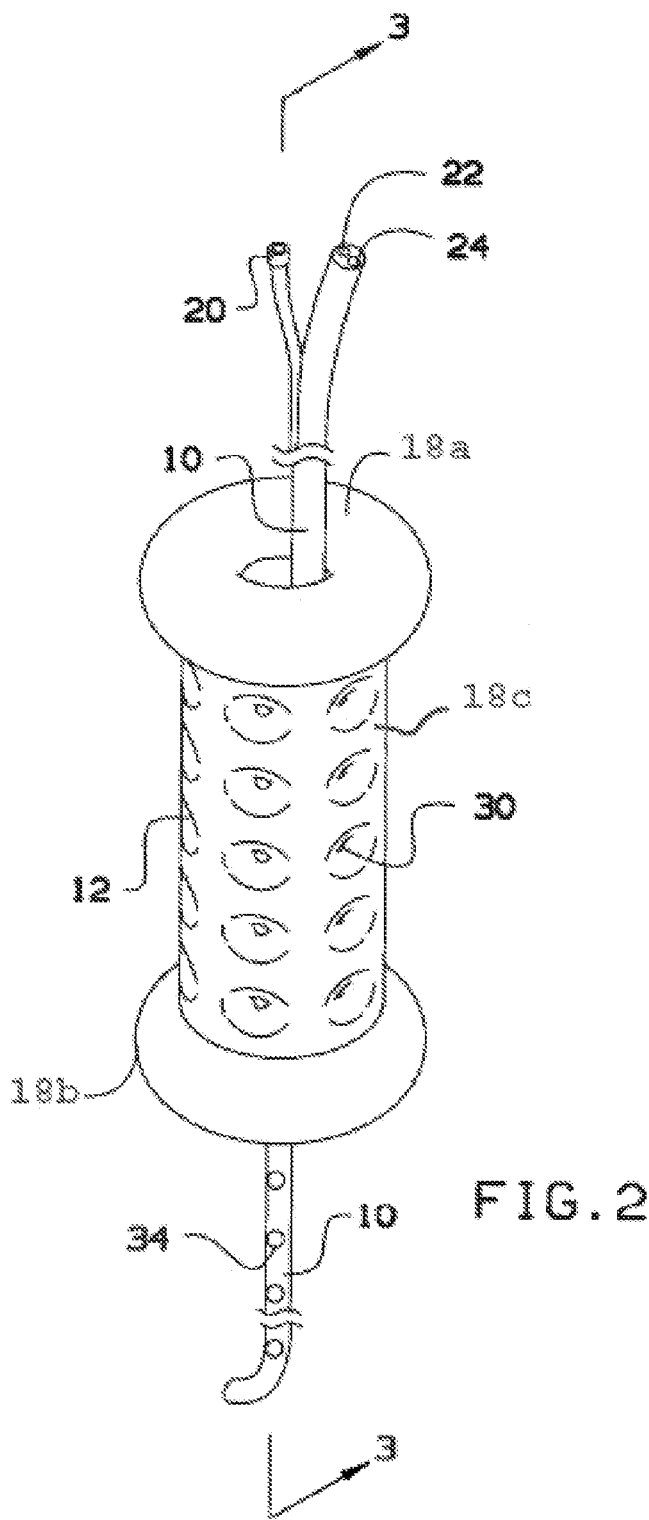
FIG. 2 is a perspective view of the device of FIG. 1.
Figure 3:
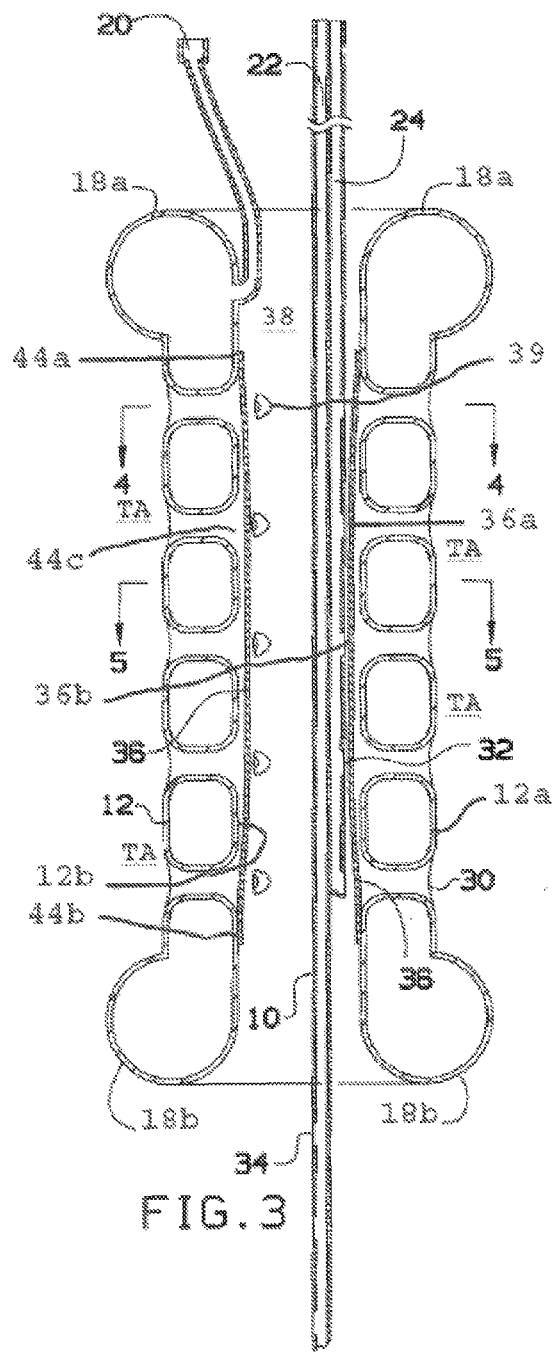
FIG. 3 is a sectional detail view of the device of FIG. 1, taken along line 3-3 in FIG. 2.
Figure 4:
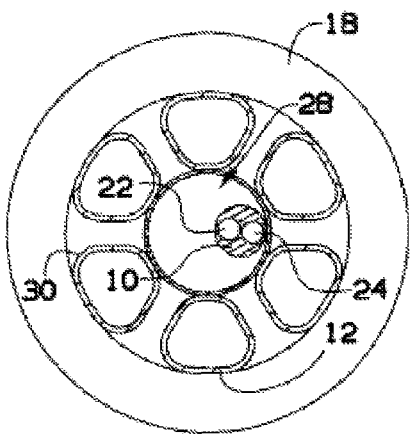
FIG. 4 is a sectional detail view of the device of FIG. 1, taken along line 4-4 in FIG. 6.
Figure 5:
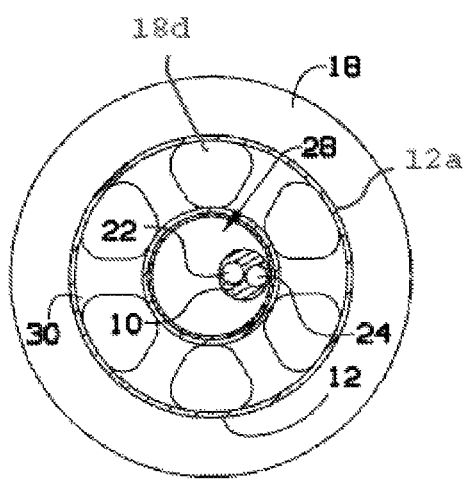
FIG. 5 is a sectional detail view of the device of FIG. 1, taken along line 5-5 in FIG. 6.
Figure 6:
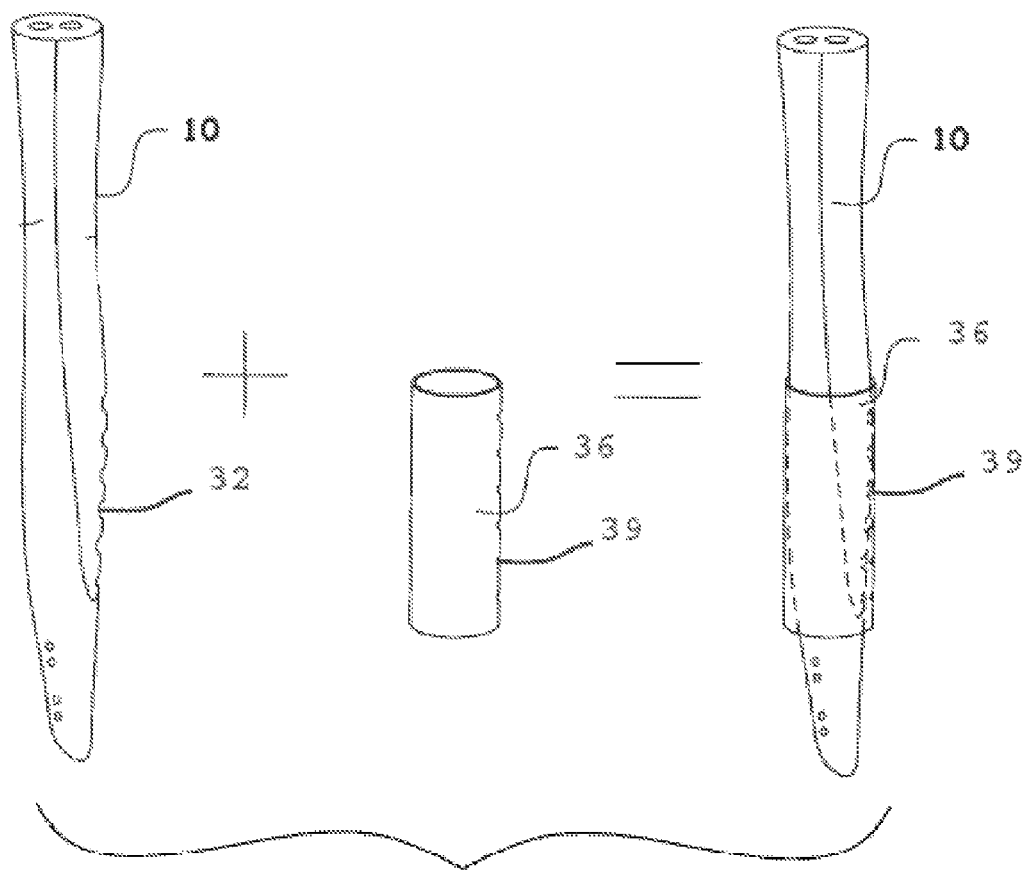
FIG. 6 is a schematic view of a device according to the present disclosure.

10: is an intraluminal hollow tube.
12: is an inflatable hollow multi-perforated stent.
12*a*: is an external surface of the stent.
12*b*: is an internal surface of the stent.
14: is a duodenum.
16: is an angle of His staple line dehiscence site.
18*a*: is a proximal ring portion of the stent.
18*b*: is a distal ring portion of the stent.
18*c*: is an intermediate portion of the stent.
18*d*: is the plenum of the stent, which includes the volume within the stent.
TA: is a target area of a bodily lumen into which the stent can be deployed, the target area defined by the proximal and distal ring portions of the stent and the external surface of the intermediate portion of the stent.
20: is a stent port for inflating the stent.
22: is a distal feed lumen.
24: is a negative pressure lumen.
26: is a gastrointestinal wall.
28: is a central lumen for the passage of gastro-intestinal fluids therethrough.
30: is a stent passage.
32: is a negative pressure tube hole.
34: is a distal feed lumen hole.
36: is a liner.
36*a*: is an external surface of the liner.
38: is a lumen of the stent
39: is a liner hole.
44*a*: is a proximal attachment point of the liner to the internal surface of the cylindrical.
44*b*" is a distal attachment point of the liner to the internal surface of the cylindrical.
44*c*: is area defined by the external surface of the liner and the internal surface of the stent.

DETAILED DESCRIPTION

Reference will now be made in detail to exemplary aspects of the present invention which are illustrated in the accompanying drawings. Wherever possible, the same reference numbers will be used throughout the drawings to refer to the same or like parts.

The present disclosure relates to device such as an intraluminal balloon stent that would potentially allow for a controllable and low pressure secure seal at the proximal and distal aspect of the stent thus better isolating an injury or dehiscence site from the remaining GI tract and allow for forward flow of oral intake. This device may allow for an alternative approach to staple line dehiscence or leakage allowing a simpler and more feasible option for physicians and their patients in resolution. Furthermore, a most distal aspect of this device might permit for distal feeds and improved nutrition instead of intravenous administration of nutrition with its possible resultant complications. Most importantly, the addition of negative pressure to the outside perimeter of the balloon stent would allow for active healing to occur and limit the complication and resources utilization considerably. The addition of a bio-absorbable mesh may improve the application of intraluminal negative pressure.

The present application is further directed toward a medical device or catheter that may consist of three hollow inflatable balloons (two hollow inflatable rings connected by a central hollow, preferably more rigid inflatable cylinder balloon) comprising a stent with an opening or a lumen of a varying diameter depending on the location and indication of the intervention. This inflatable stent may be attached to and inseparable from an intraluminal tube having a single plastic layer with radio opaque marking at the level of balloon stent attachment. Furthermore the inflation port may preferably reside along the proximal length of this intraluminal tube.

The catheter of the present disclosure will preferably have two lumens. One lumen will preferably exit at the most distal end of the catheter with multiple side perforations for possible distal feeding purposes and the other lumen will preferably exit into the outside periphery of the cylinder balloon for purposes of providing suction and negative pressure application between the device and the wall of the mucosa of the portion of the GI tract where the device is positioned.

Due to the diversity of applications and treatment population, varying lengths and volume capacities may be necessary for optimal performance. These length and volume variables may include but are not limited to, the total length of the catheter, the distal most length of the post balloon portion of the catheter, volumetric capacity and size of the ring balloons, and the length, diameter and capacity of the cylinder balloon.

Optional applications for an outside perimeter of the cylinder balloon may include the addition of a bio-absorbable mesh or widely available hemostatic agent which could act as a sponge for improved negative pressure and decreased direct mucosal suction injury.

The device of the present disclosure differs from conventional GI tract catheters and balloon stents in numerous ways, such as but not limited to:
1. Promoting active healing with negative pressure ability.
2. Distal feeding ability.
3. Involves only soft plastic components.
4. Utilizes air insufflation of balloons instead of self-expandable metals.

The device of the present disclosure is an improvement on conventional GI tract catheters and balloon stents in at least the following ways:
1. More cost effective/economic.
2. Highly reproducible with many possible physicians performing intervention.
3. Decreased complication rates including migration, erosion, obstruction and inability of removal.
4. Doesn't necessary require endoscopy for placement, re-positioning or removal.
5. Hastens the healing process and potentially shortens the disability of the patient.
6. Controllable and tighter proximal and distal seal of the stent.

The device of the present disclosure may include but is not limited to the following elements or features:
1. A dual lumen catheter 10 of varying length depending on the site and indication of the treatment. One lumen 20 of the catheter may have a proximal port with its effect at the outside perimeter of the multiperforated cylindrical balloon allowing for suction to be applied to a space between the multiperforated cylindrical balloon portion defining a single plastic layer and the interior of the GI tract where the device is positioned. The other lumen 22 and 24 of the catheter may include a distal port exiting at a distal-most aspect of the catheter and will function as infusion or suction of the lumen on the hollow viscera in which the catheter is placed. This tube will preferably exit the nose from the proximal GI tract and anus from the distal GI tract. The single plastic layer may be attached to the proximal and distal ring balloons and to dual lumen catheter so that the single plastic layer may share the side perforations of the proximal port of the dual lumen catheter.
2. Two hollow inflatable ring balloons 18 of varying volume interconnected with a more rigid hollow multiperforated cylinder balloon 12 of varying length which is accessible via the intragastric tube or catheter 10 mentioned in 1.
3. An absorbable mesh may be included on an exterior of balloon 12 to increase effectiveness of the application of negative pressure or suction.

The various elements of the device of the present disclosure may be related as follows:

Each component may be attached and inseparable. The intraluminal tube may have radiologic markings at the site of proximal and distal attached inflatable ring balloons for accurate positioning under radiologic guidance. The catheter may be positioned through the lumen of the hollow ring/cylinder balloons to limit the direct contact and potential damage to the wall of the stomach/colon. A suction only port may be effective at the outside of the hollow inflatable cylinder balloon and the wall of GI tract. Furthermore, this is the site of the potential absorbable mesh for added negative pressure effect and limitation of suction injury and improved tissue healing.

The device of the present disclosure may be used in the following exemplary manner but it is not intended to limit the use of the device to solely this illustrative example:

The device may be positioned within the lumen of the stomach and will bypass the area of extravasation illustrated on the previously performed radiologic study or endoscopy identifying the dehiscence. The device may be positioned under guidance allowing the area of extravasation of contrast to be between the radio opaque markings on the catheter. Once in place, the balloons may be inflated and negative pressure applied to the outside of the hollow cylinder balloon (between the hollow ring balloons) and thus isolate and bypass a dehiscence 16 and promote active healing of the injured tissue with negative pressure. The device of the present disclosure may be secured to the nose of the patient for immobility as well as the negative pressure which will aid in limiting its mobility and displacement. The balloons may be deflated at set time intervals to study the injured tissues response and/or extravasation of contrast. Once dehiscence has resolved, such as by being illustrated by lack of extravasation of contrast with all balloons deflated, then the device may be removed and discarded.

A device according to the present disclosure may be constructed in the following illustrative manner. It is not intended to limit the scope of the present disclosure to this exemplary approach to construction and it is intended that the present application may encompass other approaches and techniques of construction.

Plastic inflatable hollow ring balloons with connecting hollow multiperforated cylinder balloon make up the inflatable stent which is connected to the single plastic layer at the proximal and distal ring balloons. The single plastic layer may be connected to the dual lumen catheter and share the proximal port side perforations. The catheter lies within the lumen of the balloon stent and thereby limits its contact of the visceral wall/mucosa. An absorbable mesh is an option to be added or deemed necessary on the outside perimeter of the hollow cylinder balloon to aid in the negative pressure to be applied.

Silicone molds may be used to individually form all of the inflatable items and then items may then be fused together.

Many applications can be used regarding biologic tissue to periphery of hollow cylindrical balloon allowing for a tissue allo-, xenograft for tissue deficiencies. Other applications might include the application of tissue sealants via proximal lumen and applied at level of dehiscence of staple line/leakage site.

The following is an illustrative example of how the device of the present disclosure might be used. It is not intended to limit the scope of use of a device according to the present disclosure to this exemplary approach.

Trained physicians may apply this device adjacent to proximal or distal GI tract wall perforations allowing limitation of spillage or contamination of the abdominal cavity with the inflation of the balloon stent at the site of the injury and concurrently be involved in active healing process using the negative pressure application.

The device may also be used in the case of a staple line dehiscence from a gastric sleeve, for isolation of injury, reduction of pressure at site of injury and negative pressure application at site of injury to quicken the healing process. The device may allow for easy insertion and positioning (and/or re-positioning) and distal feeds if necessary. These positioning or re-positioning actions may be performed under guidance through use of but not limited to radioimaging.

This device may be used by ER, radiologist, GI, general, colorectal, thoracic or bariatric surgeons under conscious sedation or general anesthesia via nasogastric or colorectal route to apply negative pressure at a dehiscence site and allow for isolation/diversion of area. This device may be used in prevention and/or therapeutically in esophageal or distal colo anal anastomosis thereby avoiding the complication of dehiscence of staple line.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

What is claimed is:

1. A system for permitting the confined and controlled treatment of a target area [TA] of an internal body lumen using negative pressure applied to the target area [TA], the system being configured to permit target area treatment to proceed without interrupting the flow of bodily fluid through the body lumen, the system comprising:
    a resilient stent [12] having a generally elongate shape with a longitudinal axis from a proximal end to a distal end, the resilient stent having an external surface [12a], and an internal surface [12b], the stent [12] comprising an inflatable proximal portion [18a], an inflatable distal portion [18b], and an inflatable intermediate portion [18c], the proximal, distal and intermediate portions defining a single plenum [18d] into which air may be directed to cause inflation of the proximal, distal, and intermediate portions, the intermediate portion comprising a plurality of passages [30] extending from the external surface [12a] to the internal surface [12b] to permit the passage of fluid from the target area fluid through the passages separated in a sealed manner from any air in the plenum [18d] so that when the single plenum defined by the proximal, distal, and intermediate portions is inflated, the target area fluid may still flow through the passages [30] without impacting the inflated plenum, the passages configured to permit an area adjacent the external surface of the stent to be in fluid communication with an area adjacent the internal surface of the stent through the passages;
    a perforated resilient liner [36] configured to be secured to the internal surface [12b] of the stent at a proximal end [44a] and distal end [44b] of the liner, the liner [36] defining a wall having an external surface [36a], an internal surface [36b], and a plurality of liner holes [38] therethrough between proximal and distal ends of the liner, the liner holes arranged generally linearly between the proximal [44a] and distal [44b] ends of the liner [36], the liner configured such that when the liner is secured to the stent [12] the external surface [36a] of the liner is adjacent the internal surface [12b] of the stent but separated therefrom so that an area [44c] is defined by the internal surface of the stent and the external surface of the liner, the internal surface of the liner defining an internal stent area through which body lumen fluid may flow longitudinally within the generally elongate stent separate from any fluid flowing between the passages and separate from any air within the plenum; and
    a catheter tube [10] comprising a lumen [24] and having a proximal end, a distal end, and a plurality of catheter tube holes [32] positioned between the proximal and distal ends of the catheter tube, the catheter tube holes configured to be secured to the liner holes [38] along the internal surface of the liner in a sealable manner so that the lumen of the catheter tube may be in fluid communication with the stent passages;
    whereby the system is configured so that (a) the system may be delivered into the internal body lumen, (b) the plenum may be inflated so as to seal off a target area [TA] within the body lumen with the target area [TA] defined generally by the proximal and distal portions of the stent at proximal and distal ends of the target area [TA], respectively, and by the body lumen wall and the external surface of the stent along the sides of the target area [TA], and (c) a negative pressure may be applied to the lumen of the catheter tube from a source connected to the proximal end of the catheter tube so as to create a negative pressure environment in the target area [TA] of the body lumen without impacting the inflated plenum and without impacting the ability of body lumen fluid to flow through the internal area of the stent, thereby permitting therapy to proceed without disrupting the natural flow of bodily fluids or the delivery of nutrients within the body lumen during therapy.

2. The system of claim 1, wherein the passages of the intermediate portion of the stent are arranged in a circumferential array radially positioned about the stent permitting a substantially even distribution of negative pressure to the target area.

3. The system of claim 1, wherein the catheter tube [10] further comprises a second lumen [22] for directing nutrient fluids into the body lumen during treatment.

* * * * *